United States Patent [19]

Laboureau

[11] Patent Number: 5,573,538
[45] Date of Patent: Nov. 12, 1996

[54] ANCILLARY INSTRUMENT SET FOR THE RECONSTRUCTION OF THE POSTERIOR CRUCIATE KNEE LIGAMENT

[75] Inventor: Jacques P. Laboureau, Dijon, France

[73] Assignee: Societe Lars S.A., Arc-sur-Tille, France

[21] Appl. No.: 351,404

[22] PCT Filed: Jun. 23, 1993

[86] PCT No.: PCT/FR93/00627

§ 371 Date: Feb. 17, 1995

§ 102(e) Date: Feb. 17, 1995

[87] PCT Pub. No.: WO94/00057

PCT Pub. Date: Jan. 6, 1994

[30] Foreign Application Priority Data

Jun. 23, 1992 [FR] France ..................... 92 07786

[51] Int. Cl.⁶ .................................................. A61B 17/17
[52] U.S. Cl. ............................................. 606/96; 606/86
[58] Field of Search .................... 606/96, 97, 98, 606/103, 86, 87, 88

[56] References Cited

U.S. PATENT DOCUMENTS

| | | |
|---|---|---|
| 4,535,768 | 8/1985 | Hourahane et al. |
| 4,787,377 | 11/1988 | Laboureau . |
| 4,945,904 | 8/1990 | Bolton et al. . |
| 5,112,335 | 5/1992 | Laboureau et al. . |
| 5,116,372 | 5/1992 | Laboureau . |
| 5,324,296 | 6/1994 | Laboureau et al. . |
| 5,330,468 | 7/1994 | Burkhart .................... 606/96 |
| 5,350,383 | 9/1994 | Schmieding et al. ............ 606/96 |

FOREIGN PATENT DOCUMENTS

| | | |
|---|---|---|
| 0253688 | 1/1988 | European Pat. Off. . |
| 2104392 | 3/1983 | United Kingdom . |
| 91/06250 | 5/1991 | WIPO . |

*Primary Examiner*—Michael Powell Buiz
*Assistant Examiner*—Scott B. Markow
*Attorney, Agent, or Firm*—Greenblum & Bernstein P.L.C.

[57] ABSTRACT

Ancillary instruments for the reconstruction of a posterior cruciate knee ligament by drilling one or two tibial canals using a surgical operation performed from the front. The instrument set includes a system for protecting the posterior surface of the upper tibia end and an aiming device for guiding at least one drill. The protection system comprises at least one bent tube removably coupled by an extension portion to a locking handle for securing the tube through the intercondylar fossa of the femur on the posterior surface of the upper end of the tibia, so that the distal end of the bent tube serves as the stop to the drill guided by the aiming device and emerging from the tibial bone canal, and the bent tube can form, together with a rectilinear wire feed-through tube disposed in the place of the drill, a continuous canal for guiding a metallic loop used to draw the prosthetic posterior cruciate knee ligament from the anterior surface of the tibia to the femur insertion point.

20 Claims, 3 Drawing Sheets

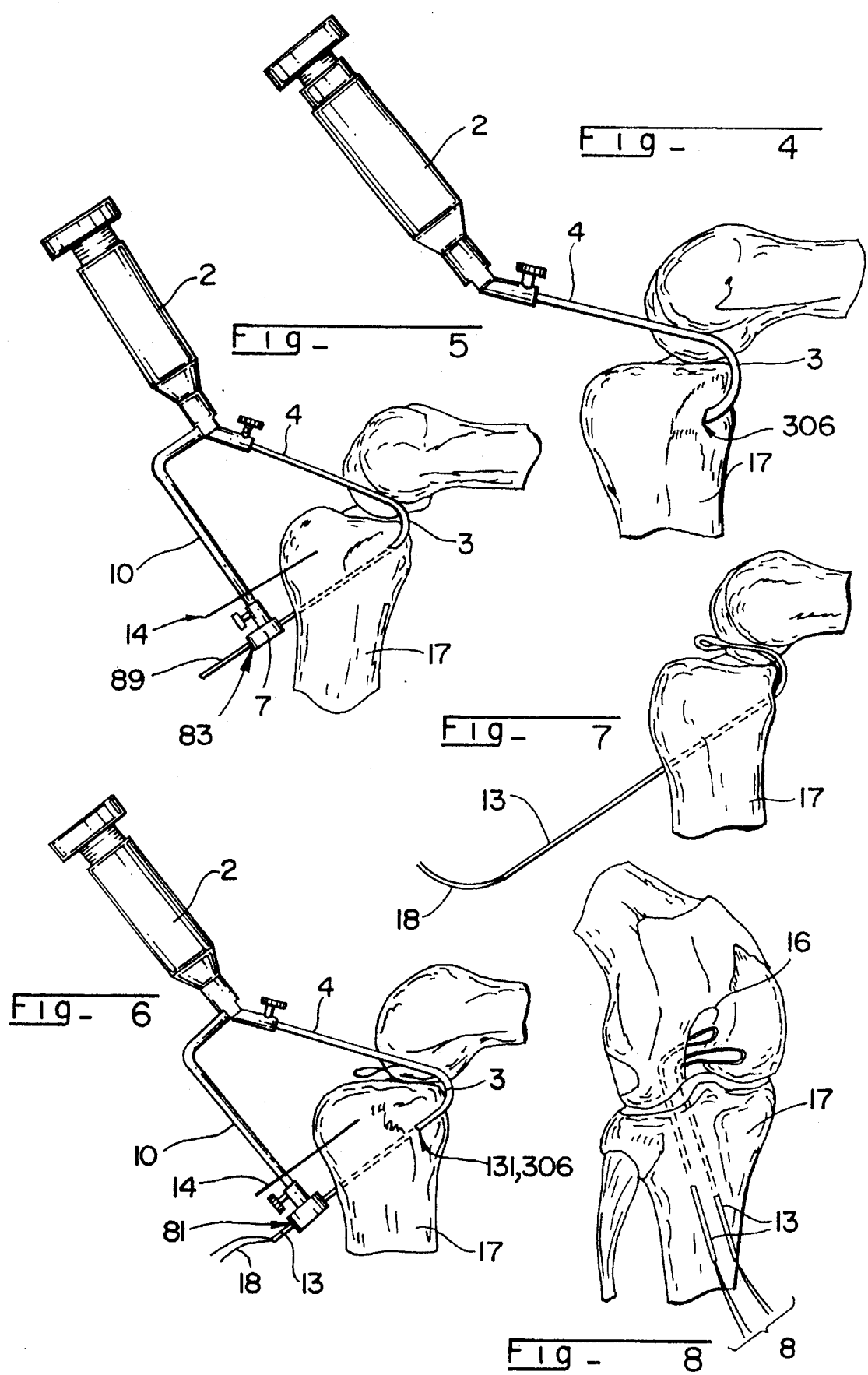

ANCILLARY INSTRUMENT SET FOR THE RECONSTRUCTION OF THE POSTERIOR CRUCIATE KNEE LIGAMENT

BACKGROUND OF THE INVENTION

1. Field of the Invention

The present invention relates to an ancillary instrument set for the reconstruction of the posterior cruciate knee ligament by drilling one or two parallel tibial insertion channels.

2. Discussion of Background Information

Generally, the posterior cruiate knee ligament is reconstructed by inserting a synthetic ligament or one or more natural tendons after drilling one or two tibial channels from front to back. It is necessary to check the exit point to avoid damaging the popliteal vascular and nerve structures during drilling.

This essential precaution entails either checking by a supplementary posterior surgical operation, or using a protective system that is introduced from the front into the intercondylar fossa to meet the posterior surface of the upper end of the tibia. Nowadays, the posterior cruciate knee ligament can also be reconstructed routinely under open surgery or more effectively using an arthroscope without arthrotomy.

It will be seen in this context that reconstruction using an arthroscope makes a cedain number of demands on the system for locating and fitting the posterior cruciate ligament. In particular, it is necessary to have an anatomically correct profile for the protective element as well as ensure that the dimensions of the protective elements are adapted to the narrowness of the front entry so that the protective element of the instrument can remain fixed in place while drilling the two parallel tibial insertion channels.

There is at least one ancillary instrument set for fitting posterior cruciate knee ligaments. This is an instrument that comprises a relatively wide, italic "S" shaped spatula which forms the rear protective element within the articulation, and which is used together with the support arm of a aiming block with two parallel drill tubes. When the support arm has been mounted on the handle of the instrument, the aiming tubes direct the drills to meet the distal end of the spatula. Using this wellknown frontal approach, the spatula is introduced through the intercondylar fossa to behind the posterior surface of the tibia. This protects the popliteal vascular and nerve structures while drilling the tibial insertion channels used for attaching the internal posterior and external posterior ends of the prosthetic ligament that is used for repairing the posterior cruciate knee ligament.

This design of spatula has a number of drawbacks, in particular:

the spatula, approximately 14 mm, is too wide and, when this spatula is introduced through the intercondylar fossa, it displaces all the capsule and ligament structures from the posterior surface of the tibia.

it is not always easy, and indeed sometimes proves impossible, to introduce the two parts of the ligament into the tibial channels and then to slide them along the special groove on the internal surface of the spatula. For the reason described above, the spatula is very often encumbered with fibrous tissues that have been displaced while it is being introduced to the posterior surface of the tibia. Recovery of the sheathed metallic wire that is used to pull the prosthetic ligament into its final position is, therefore, made very unpredictable.

furthermore, this type of ancilliary instrument has been designed exclusively for ligment reconstructions of the posterior cruciate knee ligament under open surgery, and it is not at all suitable for fitting the posterior cruciate knee ligament using an arthroscope as is widely used today. It is generally accepted that a reconstruction using an arthroscope causes considerably less trauma than a classic operation, to the extent that fitting a posterior cruciate knee ligament using an arthroscope could become part of a mobile surgical service.

SUMMARY OF THE INVENTION

It is an object of the present invention to remove these drawbacks by providing an ancillary instrument set for the reconstruction of the posterior cruciate knee ligament comprising an aiming device for alignment and guiding a drill intended for drilling one or two channels for inserting the posterior cruciate knee ligament through the tibia by means of an operation performed from the front. The instrument set includes a system for protection when the tip of the drill emerges from the posterior surface of the upper end of the tibia and is characterized by a locking handle having at its distal end:

firstly, at least one bent, hollow tube mounted on an extension which leaves the ends of the bent tube(s) free. The extension fixes rigidly into the handle to which it is fixed by a locking screw. The bent tubes are curved in such a way that they can form together with a rectilinear wire guide tube which replaces the drill after the transtibial channel(s) have been drilled, a continuous channel for guiding a metallic loop used to draw the posterior cruciate knee ligament from the anterior surface of the tibia to the femur insertion point.

and, secondly, a mounting arm at the end of which is fixed a block with parallel drill tubes aligning and guiding the drill and the wire guides in the same plane perpendicular to the plane defined by the axes of the handle and the extension and oriented so that the axes of the drill tubes intersect the end(s) of the bent tube(s).

Naturally, bearing in mind the above considerations, the instrument set will be different, depending on whether the reconstruction is carded out using an arthroscope or by arthrotomy. One embodiment of the present invention provides an instrument set specifically intended for open surgery. This comprises two bent tubes, hereinafter called "guide tubes" which are intended to be introduced through the intercondylar fossa behind the posterior surface of the upper end of the tibia. These two guide tubes are located side by side in approximately parallel planes in such a way that their distal ends are separated from each other by approximately the same distance as the two tibial insertion channels.

The two guide tubes are joined at their near end by an extension which is preferably straight and can be removed from the distal part of the handle of the instrument set. It is linearly adjustable, preferably at an angle which is obtuse to the axis of the handle to make it easier for the surgeon to adjust. It will be seen that the two guide tubes are located symmetrically with respect to the extension.

The two aiming tubes are, of course, located following the parallel axes in the same plane so that they are in line with the distal end of the two guide tubes.

In these conditions and following a series of operations which will be detailed hereinafter, after drilling the two tibial channels, it is easy to form a pair of continuous channels for inserting the two metallic loops, also called sheathed wires, from the anterior surface of the tibia to the intercondylar fossa which allow the prosthetic posterior cruciate knee ligaments to be drawn through.

A second main embodiment of the present invention allows the instrument set to be used for ligament reconstruction using an arthroscope. For this, the instrument set as described in the invention has only one guide tube attached to an extension similar to the extension which is attached to the end of the handle of the instrument in its stead.

It is clear that in this embodiment, the aiming block is different as it has three parallel drill tubes located in the same plane. The central tube is aligned with the distal end of the single guide tube, the two other tubes are set symmetrically with respect to the central tube at a distance of 14 mm from the latter. It is therefore possible to drill the first channel using the central guide tube.

The drill is then replaced by a wire guide tube which allows the drilling direction to be preserved for the second channel. For this, the instrument set is offset, either to the left (inwards), or to the fight (outwards) by fitting the left (or fight) drill tube of the aiming block over the wire guide tube held in the first channel. In this way, the central tube is offset to the left or fight of the first channel by 14 mm. After moving the guide tube sideways to align it with the central drill tube, a second tibial channel may be drilled parallel to the first.

Once again, the drill is replaced by a new wire guide tube to push through the second metallic loop which, like the first, is picked up in the intercondylar fossa.

Details of the operation of the instrument set in accordance with the present invention are described hereinafter. However, it should be noted that the aiming block and its mounting arm must be detachable in a direction parallel to the drill tubes so that the instrument set can be removed as described hereinafter. For one particular and very useful implementation of the present invention, a universal aiming block has been designed to allow the instrument set to be used either using an arthroscope or under open surgery. This aiming block has five parallel aiming tubes in a plane perpendicular to the plane passing through the axes of the handle and the extension holding the guide tube(s) spaced symmetrically in respect to a central drill tube located in line with the mounting arm between the aiming block and the handle of the instrument set. The two drill tubes located on either side of the central tube are used for reconstruction using an arthroscope, whereas the two outer drill tubes are used for reconstruction using an arthroscope as described hereinafter.

A final secondary feature of the instrument set in accordance with the present invention is the inclusion within the aiming block of a transverse drill tube in the same plane as, but perpendicular to, the five others. This transverse tube has a considerably larger diameter than the other tubes and could be of considerable benefit for autogenous reconstruction of the posterior cruciate knee ligament, using, for example, natural tendons or ligaments. The drilling block is, therefore, provided with a 90° rotation about the support arm in the plane of the drill tubes.

BRIEF DESCRIPTION OF THE DRAWING

Other features and advantages of the present invention will emerge from the description that will follow of two preferred methods of setting up an ancillary instrument set for fitting a posterior cruciate knee ligament, given as examples, not limiting the applicability of the invention, referring to the attached drawings, of which:

FIG. 1a shows a partial left view of the guide tubes for two-tube version intended for a ligament reconstruction by arthrotomy;

FIG. 1b is a partial view from below the guide tubes, whose ends are shown aligned with the drill tubes of the aiming block, which aiming block is shown from below in section through the axes of the drill tubes;

FIG. 4 is a schematic lateral view of the femur-tibia articulation showing the first stage of fitting a prosthetic posterior cruciate knee ligament using an arthroscope. This view shows the positioning of the guide tube pressing on the posterior surface of the upper part of the tibia;

FIG. 5 is the same lateral view as FIG. 4 but shows the second stage of fitting a posterior cruciate knee ligament, namely drilling the first tibial insertion channel;

FIG. 6 is a schematic lateral view of the next stage of fitting a posterior cruciate knee ligament, namely offsetting the instrument set for drilling the second tibial insertion channel, the first channel acting as axial reference for the aiming block;

FIGS. 7 and 8 are, respectively, schematic lateral and anterior views of the femur/tibia articulation, showing the position of the sheathed metallic wires passing through the tibial insertion channels.

DETAILED DESCRIPTION OF THE PREFERRED EMBODIMENTS

Figure 1:
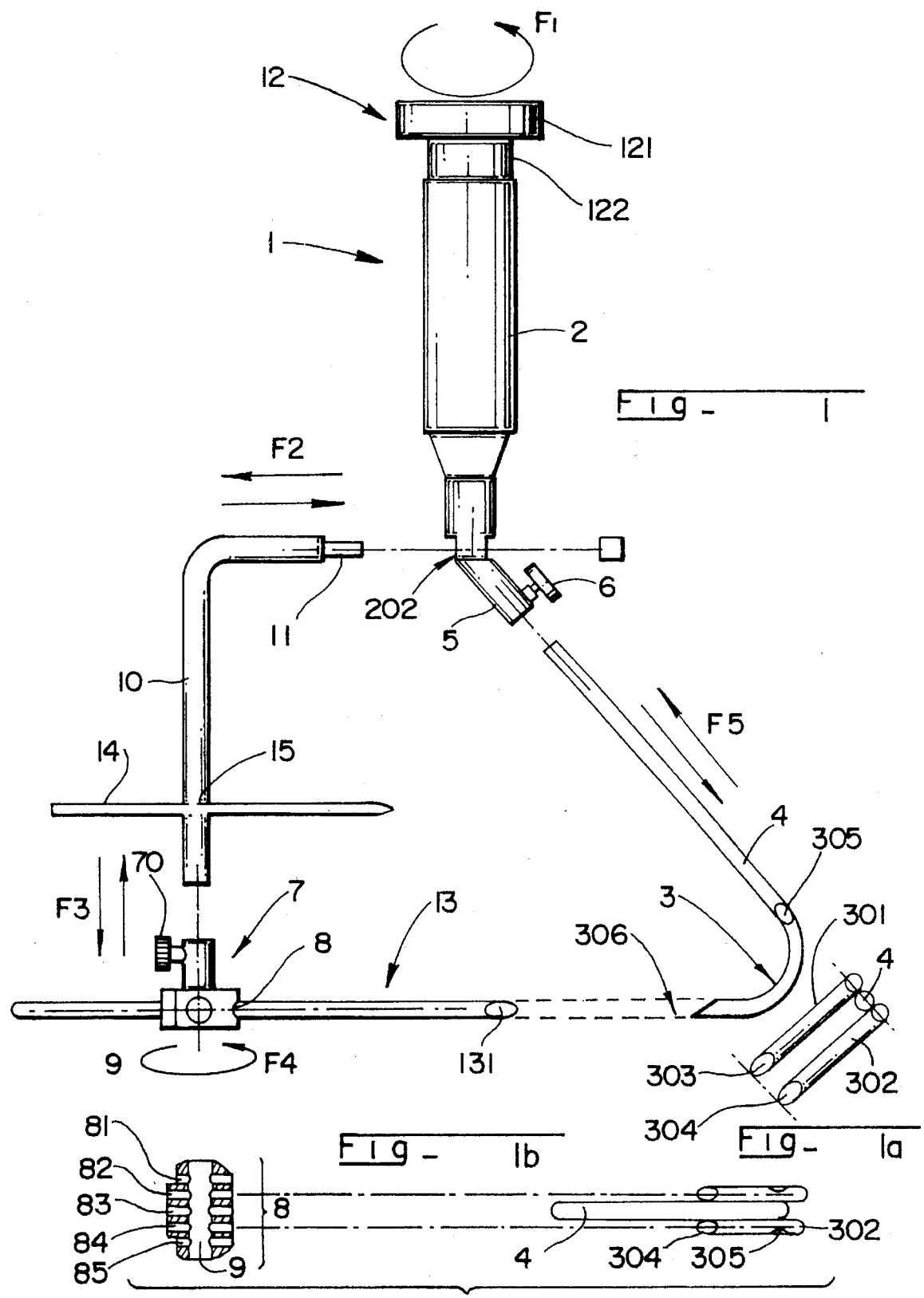
FIG. 1 is an exploded view of the ancillary instrument set according to the present invention, showing a first view of all elements of the instrument set.

The ancillary instrument set 1 in accordance with the present invention as shown in FIG. 1 comprises a lockable handle 2 to which are attached, on one side, a set of guide tubes 3 mounted on an extension 4 which is joined to the handle using a socket 5 with a locking screw 6, and on the other side an aiming block 7 with parallel drill tulles 8 in a plane perpendicular to the plan defined by the axes of the handle 2 and the extension 4 and, additionally a drill tube 9 in the same plane but perpendicular to the first tubes 8. The aiming block 7 is set on one end of a mounting arm 10 the end other of which has a square fitting 11 that is inserted in the far end 202 of the handle 2 in such a way that the mounting arm 10 has no degree of freedom with respect to the handle 2. The square fitting 11 of the mounting arm 10 that is inserted into the socket 202 of the handle 2 is locked by a longitudinal ram 12 operated by a knurled knob 121 that is attached to a threaded shaft 122. By rotating the knob 121, the longitudinal ram is brought to bear on the upper face of the square fitting 11 of the mounting arm 10 with the result that the arm 10 is locked on the inside of the handle 2.

In accordance with the embodiment of the instrument set that is especially suited to ligament reconstruction by arthrotomy, the whole of the guide tube unit 3 as in FIG. 1a comprises two parallel bent tubes 301, 302 the upper ends of which are welded on either side of the extension 4. Each bent tube 301-302 has a distal end 303-304 which will, after introduction through the intercondylar fossa, bear on the posterior surface of the upper end of the tibia to provide a stop for the drill 89 which drills the tibial insertion channels. Preferably, the other ends of the bent tubes 301-302 are bevelled laterally to provide a wider exit 305 from the intercondylar fossa to facilitate the extraction of the metallic loop used to draw the ligament.

It will be seen that the distal ends 303 and 304 of the guide tubes 3 are also bevelled 306 to be absolutely certain of trapping the ends 131 of the wire guide tubes 13 inserted in the drill tubes 82 and 84 (FIG. 1b) of the aiming block 7. The ends 131 of the wire guide tubes 13 are bullet shaped, formed by swaging, which ensures that the wire guide tubes 13 engage the guide tubes 3 satisfactorily.

Finally, a pin 14 can be inserted through a radial hole 15 in the mounting arm 10 supporting the aiming block 7 in order to immobilize the ancillary instrument set on the tibia while the surgeon is operating, as will be described hereinafter.

In accordance with one of the features of the present invention, the mounting arm 10 supporting the aiming block 7 can be removed from the handle 2 as shown in FIG. 1 by the arrows F2, simply by unscrewing the knurled knob 121 in the direction of arrow F1. Removing the mounting arm 10 in this way in the direction of F2 allows the aiming block 7 to be moved to the left of FIG. 1, sliding off the wire guide tubes 13 which must remain in place in the tibial insertion tubes, as will be described hereinafter.

In the same way, the aiming block 7 can be removed from the mounting arm 10 by unscrewing the screw 70. It is then possible to rotate the aiming block 7 by 90° bringing the drill channel 9 (FIG. 1b) in line with the bent tubes 3. When this is done, it is necessary to replace the set of guide tubes 3 in FIG. 1a which are intended for reconstruction by arthrotomy, by an assembly with a single guide tube attached to an extension of the same type as heretofore described. This single guide tube 3 will, of course, be in the median plane of the instrument set, that is exactly in line with the central tube of the aiming block, which may be the specific drill tube 9. It should be remembered in this context that the specific drill tube 9 which has replaced the central drill tube 83 by rotation about the mounting arm 10 is particularly useful for autogenous ligament reconstruction. In fact, natural tendons or ligaments intended for posterior cruciate knee ligament reconstruction are usually of a size requiring a drill tube that is approximately twice the section. It should be noted that the embodiment of the instrument set fitted with a single guide tube intended for reconstruction using an arthroscope has been intentionally omitted from FIG. 1:

as the diagram is simpler, it can easily be derived from the instrument shown.

Two examples of the typical use of the ancillary instrument set in accordance with the present invention are now given, one for ligament reconstruction under open surgery/ and the other for ligament reconstruction using an arthroscope.

Figure 2:
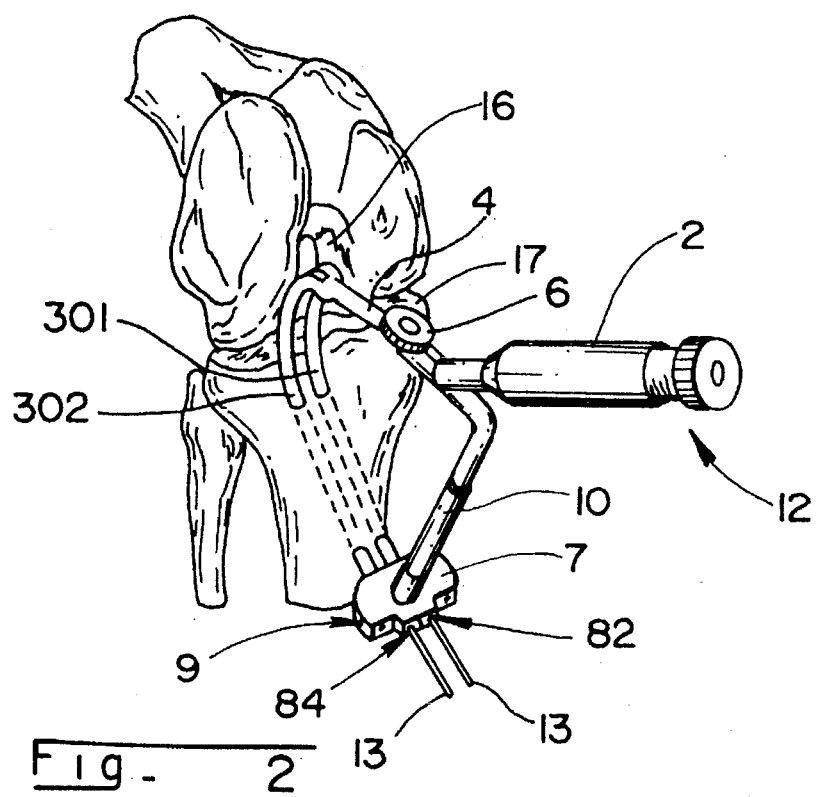
FIG. 2 is a perspective view of the femur-tibia articulation showing the instrument set as set up for fitting a posterior cruciate knee ligament by arthrotomy in accordance with the first embodiment of the present invention.
Figure 3:
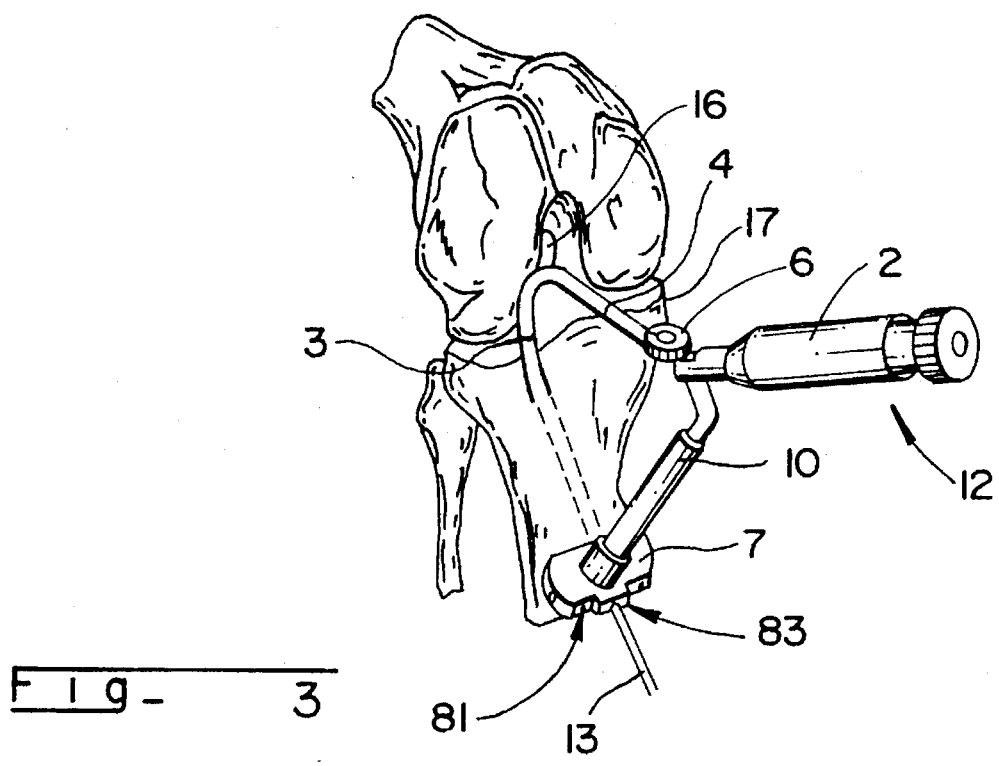
FIG. 3 is a perspective view of the femur-tibia articulation showing the instrument set as set up for fitting a posterior cruciate knee ligament using an arthroscope in accordance with the second embodiment of the present invention.

The first example of use of the ancillary instrument set in accordance with the present invention shows, with reference to FIGS. 1, 2, 7 and 8, the main stages of ligament reconstruction under open surgery. The two aforementioned guide tubes 3 are inserted through the intercondylar fossa 16 to bear against the posterior surface of the upper end of the tibia 17 (FIG. 2).

It can be seen that as the guide tubes 301, 302 are perfectly cylindrical they cause considerably less damage to the capsule and ligament structures of the posterior surface of the tibia 17 than the spatula fitted to the aforementioned known ancillary instrument. Moreover, it is particularly useful that each guide tube 301,302 helps to open up a tubular path through the nerve-free parts of the implantation zone for the internal posterior or external posterior ligament which will settle down more readily in the tubular path as it is itself approximately circular with a resultant improvement in acceptance of the prosthetic by the fibroblasts.

Using this configuration, the surgeon first inserts the guide tubes 301 and 302 through the intercondylar fossa 16 and then proceeds to locate the mounting arm 10 in the distal socket 202 of handle 2, locking it into position with the knob 121 (FIG. 1). The surgeon then attaches the aiming block 7 to the base of the mounting arm 10 using the screw 70 so that the aiming tubes 82 and 84 are in line with the distal ends 303, 304 of the guide tubes 301, 302. The whole of the instrument set thus arranged within the articulation is immobilized to the bone by introducing the pin 14 into the tibia. The surgeon can then proceed to drill the channels through the bone using the drill tubes 82 and 84, confident that the drills 89 will strike the ends 303, 304 of the guide tubes, thus avoiding damage to the surrounding tissue. The drills 89 are then withdrawn and the surgeon can insert the two wire guide tubes 13 within the two channels through the bone until the ends 131 of the wire guide tubes 13 meet the ends 306 of the guide tubes 3. The surgeon can then pass the metallic loops 18 through the channel thus formed. These can then be recovered at the exit 305 of the guide tubes 3 inside the intercondylar fossa 16. All that remains to do then is to attach the prosthetic ligament traction points to the ends of these metallic loops 18 so that the posterior cruciate knee ligament can be fitted permanently using the well-known techniques.

The second embodiment of the present invention is intended particularly for ligament reconstruction using an arthroscope and will now be described with reference to FIGS. 1 and 3 to 8. The instrument set has only one guide tube 3. The tube 3 is introduced into the femur-tibia articulation through a small incision made by the surgeon in the anterior surface of the knee in such a way that the distal end 306 of the guide tube 3 fits exactly into the intercondylar fossa 16 of the femur (FIG. 4). When the guide tube 3 is in place, the surgeon fixes the mounting arm 10 in position on the handle 2 of the instrument 1 (FIG. 5). The central drill tube 83 that is provided for this purpose in the center of the aiming block 7 allows the surgeon to locate with precision the incision point on the knee for the first tibial channel that corresponds, for example, to the external posterior cruciate knee ligament. After the drill 89 has been removed, a wire guide tube 13 is inserted as in the aforementioned variant by arthrotomy, in order to create a continuous channel through which the metallic wire 18 can be slid from the tibial entry of the channel, emerging without difficulty from the intercondylar fossa 16, to exit finally from the articulation by the small incision made for the introduction of the guide tube 3.

The mounting arm 10 of the aiming block 7 is then removed by sliding it along the wire guide tube 13. The mounting arm 10 is thus removed parallel to the direction of the first insertion channel. One of the lateral drill tubes 81 or 85 provided at the ends of the aiming block 7 is repositioned (FIG. 6). It will be noted that the two openings of the drill tubes 81 and 85 (FIG. 1b) are recessed on the aiming block 7 to provide the surgeon with a guide to avoid confusion between the drill tubes. In this operation, the single guide tube 3 must be moved sideways within the intercondylar fossa 16 so that the plane defined by the mounting arm 10 and the axis of the central drill tube 83 of the aiming block 7 remains parallel to its original position. The surgeon can then drill the second tibial insertion channel using the central drill tube 83 which corresponds, for example, to the internal posterior part of the prosthetic posterior cruciate knee ligament. The drill 89 is then replaced by a second straight wire guide tube 13, allowing a second sheathed metallic wire 18 to be passed through the new continuous channel thus created. The end loop on this second wire 18 then emerges, like the first loop, through the small incision made for the introduction of the guide tube 3. Finally, the same result is obtained as for the first embodiment as shown in FIGS. 7 and 8.

Of course, any embodiment of the form of the instrument set in accordance with the present invention which has the same essential characteristics is included within the present invention. For example, there can be variation in the angle between the handle 2 and the extension 4 or the curvature of the guide tubes 3, provided that their ends 303, 304 remain coincident with the ends 131 of the wire guide tube 13. Equally, any mechanism, apart from that which has been described, for locking the arm 10 to the handle 2 belongs to the present invention.

I claim:

1. Ancillary instrument set for reconstruction of a posterior cruciate knee ligament including protection elements when a tip of a drill emerges from a posterior surface of an upper end of the tibia in an operation performed from the anterior of the knee, said instrument set comprising:

a mounting arm comprising a far end;

an aiming device comprising an aiming block affixed to said far end of said mounting arm, said aiming block comprising parallel drill tubes for aligning and guiding the drill for drilling at least one trans-tibial channel for inserting the posterior cruciate knee ligament through the tibia;

a locking handle comprising a distal end, said mounting arm being rigidly affixed onto said handle;

an extension rigidly affixed onto said handle;

at least one wire guide tube positioned within said aiming block for replacing the drill within said aiming block and through the at least one trans-tibial channel after the channel has been drilled, said at least one wire guide tube comprising a longitudinal axis;

at least one bent, hollow tube having a first end and a distal end, said first end being affixed to said extension, said distal end extending from said extension, and said at least one bent tube is curved toward said at least one wire guide tube, to form a continuous channel for guiding a metallic loop for drawing the posterior cruciate knee ligament from an anterior surface of the tibia to a femur insertion point; and said aiming block being positioned on said mounting arm to align and guide the drill and the at least one wire guide in a plane perpendicular to a plane passing through said handle and said extension, and oriented so that the longitudinal axis of said at least one wire guide tube intersects said distal end of said at least one bent tube.

2. The ancillary instrument according to claim 1 suitable for fitting a posterior cruciate knee ligament by arthrotomy, wherein said at least one bent tube comprises two bent tubes located side-by-side in parallel planes on opposite sides of said extension.

3. The ancillary instrument according to claim 2, comprising a locking screw for rigidly and removably affixing said extension onto said handle.

4. The ancillary instrument according to claim 2, wherein said distal end of each of said two bent tubes is laterally beveled.

5. The ancillary instrument according to claim 1 suitable for fitting a posterior cruciate knee ligament using an arthroscope, wherein said at least one bent tube comprises a single bent tube attached to said extension.

6. The ancillary instrument according to claim 1, wherein said distal end of said at least one bent tube is laterally beveled.

7. The ancillary instrument according to claim 6, wherein said at least one wire guide tube has a substantially bullet-shaped end.

8. The ancillary instrument according to claim 1, wherein said parallel drill tubes of said aiming block comprise five drill tubes.

9. The ancillary instrument according to claim 8, wherein said five drill tubes comprise a central tube and four tubes symmetrically arranged on opposite lateral sides of said central tube.

10. The ancillary instrument according to claim 8, wherein two of said five drill tubes have openings that are recessed with respect to openings of the remaining three drill tubes.

11. The ancillary instrument according to claim 10, wherein said five parallel drill tubes are arranged to form an array having outer ends of mutually adjacent drill tubes, and wherein said two recessed drill tubes are positioned respective to said outer ends of said array.

12. The ancillary instrument according to claim 9, wherein two of said five drill tubes have openings that are recessed with respect to openings of the remaining three drill tubes.

13. The ancillary instrument according to claim 12, wherein said five parallel drill tubes are arranged to form an array having outer ends of mutually adjacent drill tubes, and wherein said two recessed drill tubes are positioned respective to said outer ends of said array.

14. The ancillary instrument according to claim 1, wherein said aiming block is rotatable in a plane passing through said drill tubes about an axis perpendicular to said plane around said mounting arm, and said aiming block includes an additional drill tube perpendicular to said drill tubes capable of being aligned with said distal end of said at least one bent tube.

15. The ancillary instrument according to claim 14, wherein said additional drill tube has a diameter approximately twice that of said drill tubes.

16. The ancillary instrument according to claim 1, further comprising means for enabling removal of said mounting arm from said handle by sliding said mounting arm sideways in a direction parallel to a plane passing through said drill tubes.

17. The ancillary instrument according to claim 1, wherein said mounting arm comprises a near end and a square fitting at said near end; and a socket for receiving said square fitting at said distal end of said handle, with said square fitting being positionable in said socket.

18. The ancillary instrument according to claim 17, comprising means for rigidly locking said mounting arm to said handle.

19. The ancillary instrument according to claim 18, wherein said means for rigidly locking comprise a threaded ram positionable on an upper face of said square fitting by a knob located at a proximal end of said handle.

20. The ancillary instrument according to claim 19, wherein said knob comprises a knurled knob.

* * * * *